US007429396B2

(12) United States Patent
D'Amelio, Sr. et al.

(10) Patent No.: US 7,429,396 B2
(45) Date of Patent: *Sep. 30, 2008

(54) ANTIFUNGAL COMPOSITION, ITS FUNGICIDAL EFFECT ON PATHOGENIC DERMATOPHYTES, AND PROCESS FOR INHIBITING GROWTH OF FUNGI

(75) Inventors: Frank S. D'Amelio, Sr., Huntington, NY (US); Youssef W. Mirhom, Huntington Station, NY (US)

(73) Assignee: Bio-Botanica, Inc., Hauppauge, NY (US)

(*) Notice: Subject to any disclaimer, the term of this patent is extended or adjusted under 35 U.S.C. 154(b) by 279 days.

This patent is subject to a terminal disclaimer.

(21) Appl. No.: 11/211,102

(22) Filed: Aug. 25, 2005

(65) Prior Publication Data

US 2006/0073218 A1 Apr. 6, 2006

Related U.S. Application Data

(63) Continuation-in-part of application No. 10/784,901, filed on Feb. 24, 2004, now Pat. No. 7,214,392.

(60) Provisional application No. 60/449,437, filed on Feb. 25, 2003.

(51) Int. Cl.
*A61K 36/53* (2006.01)
*A61K 36/05* (2006.01)
*A61K 36/71* (2006.01)
*A61K 36/00* (2006.01)

(52) U.S. Cl. .................. 424/745; 424/739; 424/726; 424/725

(58) Field of Classification Search ............... None
See application file for complete search history.

(56) References Cited

U.S. PATENT DOCUMENTS

| 5,906,825 | A | * | 5/1999 | Seabrook et al. ............. 424/404 |
| 6,048,836 | A | * | 4/2000 | Romano et al. ............. 510/490 |
| 6,106,838 | A | * | 8/2000 | Nitsas ........................ 424/745 |
| 6,153,208 | A | * | 11/2000 | McAtee et al. .............. 424/402 |
| 6,296,880 | B1 | * | 10/2001 | Murad ........................ 424/616 |
| 6,312,698 | B1 | * | 11/2001 | Shahi et al. ................. 424/757 |
| 6,338,855 | B1 | * | 1/2002 | Albacarys et al. ........... 424/409 |
| 6,579,542 | B1 | * | 6/2003 | Faulkner ..................... 424/726 |
| 7,214,392 | B2 | * | 5/2007 | D'Amelio et al. ........... 424/745 |
| 2001/0005510 | A1 | * | 6/2001 | Garofano .................... 424/405 |
| 2002/0034489 | A1 | * | 3/2002 | Wiegland et al. ......... 424/70.24 |
| 2002/0164386 | A1 | * | 11/2002 | Meisner .................... 424/725.1 |

FOREIGN PATENT DOCUMENTS

KR 2002057448 * 7/2002

OTHER PUBLICATIONS

Daferera et al. J. Agric. Food Chem. 2000. vol. 48, pp. 2576-2581.*
Giamperi et al. J. Essential Oil Research. 2002. vol. 14, No. 4, pp. 312-318.*
Viollon et al. Mycopathologia. 1994. vol. 128, pp. 151-153.*
Castleman, M. The Healing Herbs. 1991. Rodale Press, Emmaus, PA. pp. 115-117, 201-204,, 311-313, and 351-354.*
Janssen et al. Pharm. Weekbl. Schi. Ed. 1988. vol. 10, No. 6, pp. 277-280, DRUGU abstract enclosed.*
Alippi et al. J. Herbs, Spices, Medicinal Plants. 1996. Vo.. 4, No. 2, pp. 9-16, EMBASE abstract enclosed.*

* cited by examiner

*Primary Examiner*—Christopher R. Tate
(74) *Attorney, Agent, or Firm*—Roylance, Abrams, Berdo & Goodman, L.L.P.

(57) ABSTRACT

A natural preservative composition obtained from plant materials provides antimicrobial activity for use as an antifungal agent. The antifungal agent is effective in inhibiting the growth of *Epidermophyton floccosum, Trichophyton mentagrophytes* and *Microsporum canis*. The antimicrobial agent has a MIC as low as 0.03 μl/ml capable of inhibiting and/or killing these organisms. The antimicrobial agent includes selective mixtures of *Origanum vulgare* L., *Thymus vulgaris* L., *Cinnamomum zeylanicum* Nees, *Rosmarinus officinalis* L., *Lavandula officinalis* L., *Mentha piperita* L., *Citrus Limon* L., *Hydrastis canadensis* L. and *Olea europaea* L.

27 Claims, No Drawings

ANTIFUNGAL COMPOSITION, ITS FUNGICIDAL EFFECT ON PATHOGENIC DERMATOPHYTES, AND PROCESS FOR INHIBITING GROWTH OF FUNGI

CROSS-REFERENCE TO RELATED APPLICATION

This application is a continuation-in-part application of Ser. No. 10/784,901, filed Feb. 24, 2004, now U.S. Pat. No. 7,214,392 which claims the benefit under 35 U.S.C. § 119(e) of prior provisional application No. 60/449,437, filed Feb. 25, 2003, which are hereby incorporated by reference in their entirety.

FIELD OF THE INVENTION

The present invention is directed to a process for inhibiting the growth of fungus microorganisms and to an antifungal composition. The invention is further directed to an antifungal composition containing a mixture of plant materials that is effective in inhibiting the growth of a fungus and other microorganisms and to a method of killing or inhibiting the growth of a fungus using the mixture of plant materials. The composition of the invention is particularly effective in treating dermatophytes such as *Epidermophyton, Trichophyton* and *Microsporum*.

BACKGROUND OF THE INVENTION

Preservatives and antimicrobial agents have been used over the years to control or inhibit the growth of various microorganisms in various products and particularly food compositions. The increased use of antibiotics and antimicrobial agents and compositions has resulted in numerous pathogenic microorganisms developing new strains that are resistant to many of the commonly used antimicrobial, antifungal and antibacterial agents.

Many of the commonly used food and cosmetic preservatives and antimicrobial agents are synthetic compounds. In recent years, there has been an increased interest in avoiding or eliminating the use of synthetic compounds and in developing and promoting the use of natural materials. Plant materials are generally considered less toxic to the consumer and a more suitable natural alternative to synthetic compounds.

Various herbal and plant preparations are known for certain uses. For example, one known composition is a mixture of *Echinaceae angustifolia radix* and Plantago. This composition has been produced as an oral hygiene composition. Various reports have been produced showing antibacterial activity in the oral cavity and promoting general health of oral tissue.

Although various plant compositions have been produced, many of these have not been shown to be effective in inhibiting the growth of microorganisms. In addition, many of the commercially available compositions have not shown long antimicrobial activity. Fungal infections are common in humans, as well as other animals. The uncontrolled growth of many fungi can cause various diseases and discomfort to the animal. Topical antifungal preparations are synthetic products commonly used, although many topically applied compositions may not be effective for certain strains.

One example of a composition containing botanical materials is disclosed in U.S. Pat. No. 6,197,305 to Friedman et al. The disclosed composition is stated to have antifungal properties, prolonged antifungal activity and good antibacterial activity. The antifungal composition contains an essential oil and an herbal extract for use against fungi such as *Aspergillus niger* and *Candida albicans*.

U.S. Pat. No. 6,027,716 to Levin et al. discloses a composition containing an herbal extract and an essential oil. The components forming the resulting composition are disclosed as having a synergistic effect and antibacterial activity. The composition includes cinnamon oil as the essential oil. The herbal extract is a mixture of Plantago, Hypericum, Echinacea and Propolis.

U.S. Pat. No. 5,939,050 to Iyer et al. discloses an antimicrobial composition containing two different antimicrobial agents for use in oral hygiene products. The compositions are disclosed as being effective to inhibit the growth of bacteria, such as *Actinomyces viscosus, Fusobacterium nucleatum, Porphyromonas gingivalis, Streptococcus mutans*, and *Streptococcus sanguis*. The antimicrobial agents are plant oils and extracts and are combined to form a synergistic composition.

These compositions and preparations that have been previously available have exhibited some success. There is, however, a continuing need in the industry for an improved antimicrobial, antifungal and antibacterial composition.

SUMMARY OF THE INVENTION

The present invention is directed to a process for inhibiting the growth of various microorganisms and particularly fungi. The invention is also directed to a method and composition for inhibiting the growth of pathogenic dermatophytes. The invention is also directed to an antifungal agent and an antifungal composition obtained from plant and botanical materials and extracts. The invention is also directed to a method of treating pathogenic dermatophytes by contacting the dermatophytes with an antifungal containing a mixture of plant materials.

Accordingly, a primary aspect of the invention is to produce an antimicrobial agent and composition having antifungal properties. The composition contains an effective amount of a mixture of plant materials or plant extracts that together effectively inhibit the growth of fungi such as *Epidermophyton, Trichophyton* and *Microsporum*.

Another aspect of the invention is to provide an antifungal composition obtained from plant materials, plant extracts and/or essential oils obtained from the plant materials. In one preferred embodiment of the invention, the plant materials, plant extracts or essential oils are obtained from *Origanum vulgare* L., *Thymus vulgaris* L., *Cinnamomum zeylanicum* Nees, *Rosmarinus officinalis* L., *Lavandula officinalis* L., and *Hydrastis canadensis* L. The antifungal composition typically contains a mixture of the plant materials, plant extracts or oils in amounts effective to inhibit the growth of fungi.

The antifungal agent of the invention is particularly suitable for inhibiting the growth of fungi in various surfaces that can support the growth of microorganisms. The antifungal agent can be admixed with various compositions such as cosmetics and food products or applied to the surface of the food or other product to prolong the storage and shelf life of the food products. The antifungal agent can also be applied to the surface of the skin of an animal in need thereof to treat fungal infections.

The antifungal agent can be dispersed in a suitable carrier or vehicle for topically applying to the skin of the patient.

The aspects of the invention are basically attained by providing a process for inhibiting the growth of fungi. The process comprises the step of contacting the microorganisms or a surface containing the microorganisms with an effective amount of an antifungal composition. In one embodiment, the antifungal composition includes a mixture of plant materials comprising *Origanum vulgare* L., *Thymus vulgaris* L., *Rosmarinus officinalis* L., *Lavandula officinalis* L., and *Hydrastis*

*canadensis* L. In another embodiment of the invention, the composition also contains *Cinnamomum zeylanicum* Nees in an amount effective to provide an antifungal and stabilizing effect.

The aspects of the invention are also attained by providing a process for treating dermatophytes on the skin of an animal by topically applying an antifungal composition. The antifungal agent is comprised of a mixture of plant materials and extracts selected from the group consisting of *Origanum vulgare* L., *Thymus vulgaris* L., *Rosmarinus officinalis* L., and *Lavandula officinalis* L. A carrier for the antifungal agent is provided. The antifungal agent is present in an amount effective to kill or inhibit the growth of fungi. In one embodiment, the antifungal agent also includes a component selected from the group consisting of *Cinnamomum zeylanicum* Nees, *Hydrastis canadensis* L, *Olea europaea, Mentha piperita* L., *Citrus Limon* L., and mixtures thereof.

These and other aspects of the invention will become apparent from the following detailed description of the invention which disclose various embodiments of the invention.

DETAILED DESCRIPTION OF THE INVENTION

The present invention is directed to a process and composition for inhibiting the growth of various microorganisms, and particularly fungi. The invention is particularly directed to an antifungal composition and preparation containing active components obtained from selected plant materials.

Many microorganisms are known to have an adverse effect on the health of animals, and particularly humans, as well as on the shelf life of foods and other products. The composition of the invention is effective in killing or inhibiting the growth of fungi on various substrates. The invention is particularly effective in treating fungal infections on the skin and nails of an animal.

The composition of the invention includes an antimicrobial agent in an amount that is effective in providing the desired antimicrobial inhibiting effect. The antimicrobial agent is an antifungal agent that is effective in inhibiting the growth of various microorganisms including, for example, *Staphylococcus aureus, Escherichia coli, Salmonella typhimurium, Klebsiella pneumoniae, Pseudomonas aeruginosa, Mycobacterium smegmatis, Candida albicans*, and *Aspergillus niger*. The antimicrobial agent is effective in inhibiting the growth of a broad range of gram-positive and gram-negative bacteria, acid-fast bacteria, molds, yeasts and fungi.

In one embodiment of the invention, the antimicrobial agent is an antifungal agent comprising a mixture of botanical or plant materials and extracts containing active compounds that are combined in a manner to provide antimicrobial activity. The antifungal agent is effective in killing and/or inhibiting various fungi including *Epidermophyton floccosum, Trichophyton mentagrophytes* and *Microsporum canis*. The antifungal agent of the invention is particularly suitable for inhibiting pathogenic dermatophytes. The antifungal agent and compositions containing the antifungal agent can contain the whole plant, extracts of the plant and mixtures thereof. In preferred embodiments, the botanical components are extracts, oils or fractions containing the active components. The antifungal agent in one preferred embodiment of the invention is a mixture of botanical extracts and oils of *Origanum vulgare* L., *Thymus vulgaris* L., *Cinnamomum zeylanicum* Nees, *Rosmarinus officinalis* L., *Lavandula officinalis* L., and *Hydrastis canadensis* L. With the exception of *Hydrastis canadensis* L., each of the botanical materials are present in an amount of about 5 wt % to about 40 wt % based on the total weight of the antifungal agent. Due primarily to its limited solubility, *Hydrastis canadensis* L. is included in amounts of 0.1 wt % or less, and typically 0.01 wt % or less. The botanical materials are preferably combined in synergistic amounts to attain antifungal or other antimicrobial activity for one or more target microorganisms to be inhibited.

In one embodiment, an antifungal composition is prepared from an antifungal agent including about 30 wt % *Origanum vulgare* L., about 30 wt % *Thymus vulgaris* L., about 10 wt % *Cinnamomum zeylanicum* Nees, about 20 wt % *Rosmarinus officinalis* L., about 9.998 wt % *Lavandula officinalis* L., and about 0.002 wt % *Hydrastis canadensis* L. In another embodiment, the antifungal agent consists essentially of *Origanum vulgare* L., *Thymus vulgaris* L., *Rosmarinus officinalis* L., *Hydrastis canadensis* L., and *Lavandula* L. This antifungal agent has been shown to have a Minimum Inhibitory Concentration (MIC) and a Minimum Inhibitory Fungicidal Concentration (MFC) of 0.06 µl/ml for *Epidermophyton floccosum* and *Trichophyton mentagrophytes* and a MIC and MFC of 0.015 µl/ml for *Microsporum canis*.

In another embodiment, the antifungal agent consists essentially of *Origanum vulgare* L., *Thymus vulgaris* L., *Rosmarinus officinalis* L., *Lavandula officinalis* L., *Hydrastis canadensis* L., and *Olea europaea* L. This antifungal agent has been found to exhibit a MIC and MFC of 0.06 µl/ml for *Epidermophyton floccosum* and 0.125 µl/ml for *Trichophyton mentagrophytes* and *Microsporum canis*.

In a further embodiment, the antifungal agent consists essentially of *Origanum vulgare* L., *Thymus vulgaris* L., *Cinnamomum zeylanicum* Nees, *Rosmarinus officinalis* L., *Lavandula officinalis* L., *Hydrastis canadensis* L., *Olea europaea* L., *Mentha piperita* L., and *Citrus limon* L. This antifungal agent has been found to exhibit a MIC and MFC of 0.125 for *Epidermophyton floccosum* and an MIC and MFC of 0.06 for *Trichophyton mentagrophytes* and *Microsporum canis*.

The antifungal agent of the invention preferably includes a mixture of the extracts to provide antifungal amounts of caracrol, thymol, cinnamaldehyde, eugenol, cineole, camphor, α-pinene, rosmarinic acid, linalol, linalyl acetate, berberbine, hydrastine, oleuropein, menthol, menthyl acetate, menthone, limonene, geranial, neral and citronellal.

In preferred embodiments of the invention, extracts of the botanical materials are mixed together in proportions to provide the desired antimicrobial activity. The ratio of the components can also be adjusted to increase the antimicrobial activity or selectivity for a target microorganism. In various embodiments of the invention, the antibacterial composition contains about 20 to 40 wt % *Origanum vulgare* L., about 20 to 40 wt % *Thymus vulgaris* L., about 5 to 15 wt % *Cinnamomum zeylanicum* Nees, about 10 to 30 wt % *Rosmarinus officinalis* L. and about 5 to 15 wt % *Lavandula officinalis* L. In one preferred embodiment, the antimicrobial composition also contains about 0.001 to about 0.01 wt % and typically about 0.001 wt % to 0.003 wt % of *Hydrastis canadensis* L. A particularly suitable antimicrobial composition comprises about 30 wt % *Origanum vulgare* L., about 30 wt % *Thymus vulgaris* L., about 10 wt % *Cinnamomum zeylanicum* Nees, about 20 wt % *Rosmarinus officinalis* L., about 0.002 wt % *Hydrastis canadensis* L., and the balance (about 10 wt %) *Lavandula officinalis* L.

In one preferred embodiment, the antifungal agent includes about 20 wt % to about 40 wt % *Origanum vulgare* L., about 20 wt % to about 40 wt % *Thymus vulgaris* L., about 10 wt % to about 30 wt % *Rosmarinus officinalis* L., and about 5 wt % to about 15 wt % *Lavandula officinalis* L. The antifungal agent can also contain about 0.001 wt % to about 0.01 wt % *Hydrastis canadensis* L., about 0.001 wt % to about 0.005 wt % *Olea europaea* (olive leaf extract), and mixtures thereof. In further embodiments, the antifungal agent can include an effective amount of *Cinnamomum zeylanicum* Nees (cinnamon bark extract) to inhibit the growth of certain fungi. The *Cinnamomum zeylanicum* Nees is typically included in an amount of about 5 wt % to 15 wt %, and preferably about 10 to 15 wt % based on the total weight of the antifungal agent. In other embodiments, the antifungal agent includes about 1 wt % to about 5 wt % *Mentha piperita* L. and about 1 wt % to 5 wt % *Citrus Limon* L.

The botanical materials can be used in the form of the leaves, flowers, stems of the plant and mixtures thereof that have been dried and reduced to fine particles or powders. The plant materials can be reduced by grinding and pulverizing, followed by maceration. The dried plant materials can be mixed in a suitable mixing or blending apparatus and used as a dry or substantially dry powder. In other embodiments, the powder can be dispersed in a suitable carrier or vehicle that can be applied to the environment or surface where the antimicrobial and antifungal effect is desired.

In one preferred embodiment, the botanical materials are in the form of an extract or essential oil obtained from the plant materials. One or more of the botanical materials can be provided in the form of an extract or essential oil that is combined with a dry powder of the remaining plant materials. The extracts and essential oils are generally a mixture of esters, aldehydes, alcohols, ketones and terpenes obtained from the botanical materials. The essential oils can be prepared by a number of known processes that are able to recover the essential oils and active compounds from the plant materials.

One suitable process for preparing the extracts is by subjecting the plant materials to a distillation process. In this process, the plant material is macerated and heated in an amount of water for sufficient time. The resulting mixture is then distilled with steam to remove the organic components with the steam. The steam and organic components are then condensed and collected in a suitable collection vessel. The resulting oil phase is then separated from the aqueous phase by standard separation processes. The essential oil component is then purified as needed.

Alternatively, the botanical materials can be obtained and used as a tincture. The tincture can be obtained by extracting the active compounds using a solvent or extracting medium. The solvent can be an aqueous, organic solvent or mixture thereof. Examples of organic suitable solvents include glycerin, propylene glycol, and ethanol. In other embodiments, the extracting solvent is an aqueous/ethanol mixture that can contain about 10% to about 90% ethanol by volume. The botanical materials are generally macerated in the presence of the selected solvent. The solvent is allowed to remain in contact with the botanical materials for a suitable length of time to extract the active compounds before filtering to remove the solid materials. The filtrate is collected as the extract or tincture. The extract can be further purified and the concentration adjusted by evaporating the solvent or adding additional solvent. In one embodiment, the solvent in the tincture or extract is evaporated to obtain a residue or extract. The resulting extract can be in the form of a dry powder, oil or paste depending on the recovered fraction or compounds extracted from the botanical materials.

The extracts can also be obtained by placing the botanical materials in a column and percolating with the solvent by passing the solvent through the column. Percolation is desirable in some instances where the volume of solvent used can be minimized. The volume of solvent can be controlled by adjusting the flow rate through the column. Changing the flow rate and volume of the solvent can determine the make-up of the final extract for some plant materials that contain constituents with varying solubilities.

The extraction process can be carried out in an extraction vessel with a mixture of the plant material in hot water heated to about 90° C. for several hours, typically about 5-8 hours. The liquid material is then collected and then passed through a suitable separation column to purify the active components of the extract. Examples of separation media for use in the column include polystyrene, polyacrylic acid esters, silica gel and polymethacrylic acid esters.

The botanical materials, extracts and/or essential oils are blended in a suitable ratio to provide the desired antimicrobial and stabilizing activity for the intended use. The botanical materials contain various compounds that can have an effect on the antimicrobial properties. The antimicrobial properties can be modified by altering the ratio of the components to be more or less selective for a specific microorganism.

The plant materials, oils and extracts have been found to have a synergistic effect when combined to provide effective antimicrobial activity that is not found in the plant materials individually. The plant materials have been found to contain various compounds that when combined in the mixture of botanical materials exhibit antimicrobial properties. For example, *Origanum vulgare* L., and *Thymus vulgaris* L. contain carvacrol and thymol. *Cinnamomum zeylanicum* Nees contains primarily cinnamaldehyde and eugenol. *Rosmarinus officinalis* L. contains 1,8-cineole, camphor, α-pinene and small amounts of rosmarinic acid. *Lavandula officinalis* L. contain linalyl acetate and linalol. *Hydrastis canadensis* L contain berberine and hydrastine alkaloids. *Olea europaea* L. contains oleuropein, *Mentha piperita* L. contains menthol, menthyl acetate and menthone, *Citrus limon* L. contains limonene together with the aldehydes geranial, neral and citronellal. In one embodiment of the invention, the antimicrobial agent is a mixture of the botanical materials, extracts or essential oils to provide antimicrobial amounts of carvacrol, thymol, cinnamaldehyde, eugenol, cineole, camphor, α-pinene, rosmarinic acid, linalol, linalyl acetate, berberine, hydrastine, oleuropein, menthol, menthyl acetate, menthone, limonene, geranial, neral, and citronellal where the components are provided in an amount to obtain an antifungal or antimicrobial effect.

The *Cinnamomum zeylanicum* Nees or cinnamon bark fraction is particularly effective in inhibiting the growth of *S. typhimurium* and *P. aeruginosa* which are normally resistant to a number of common antibacterial agents. The antibacterial agent of the invention containing cinnamon bark extract was found to be effective in inhibiting the growth of *S. typhimurium* with a MIC of 0.075% and *P. aeruginosa* with a MIC of 0.15% by volume of the agar medium. The antifungal agent of the invention containing *Cinnamomum zeylanicum* Nees is particularly effective for killing or inhibiting *Epidermophyton floccosum, Trichophyton mentagrophytes* and *Microsporum canis*.

In some compositions and processes for using the compositions, it is desirable to avoid the use of cinnamaldehyde so that the cinnamon bark extract (*Cinnamomum zeylanicum* Nees) is not used in the antimicrobial agent. The antimicrobial agent without the cinnamon bark extract has been found to inhibit the growth of *S. typhimurium* at a MIC of 0.35% and *P. aeruginosa* with a MIC of 0.55% by volume based on the volume of the agar medium. An antifungal agent without the cinnamon bark extract exhibits antifungal effects for *Epidermophyton floccosum, Trichophyton mentagrophytes* and *Microsporum canis*. In embodiments where the cinnamon bark extract is not used, olive leaf extract (*Olea europaea*) can be added in an amount to enhance the antimicrobial and antifungal properties of the composition. Olive leaf extract contains Oleuropein which has been found to be a potent antimicrobial agent for some microorganisms or fungi. The olive leaf extract is only slightly soluble in the oils of the remaining extracts and is used in amounts of 1 wt % or less. Typically, the olive leaf extract is used in amounts of about 0.01 wt % or less.

In one embodiment, the antimicrobial composition is an antifungal composition comprising about 33.3 wt % *Origanum vulgare* L., about 33.3 wt % *Thymus vulgaris* L., about 22.3 wt % *Rosmarinus officinalis* L., about 0.002 wt % *Hydrastis canadensis* L., and the balance (about 10 wt %) *Lavandula officinalis* L. In a further embodiment, the composition also contains about 0.001 wt % olive leaf extract. In another embodiment, the antifungal composition comprises at least 20 wt % *Cinnamomum zeylanicum* Nees and an effective amount of *Mentha piperita* L. and *Citrus limon* L. to provide antifungal properties. The *Mentha piperita* L. and *Citrus Limon* L. are included in an amount of 10 wt % or less, and typically about 5 wt % or less.

The antifungal and antimicrobial agent containing the components of the botanical materials can be used directly as obtained or can be combined with a suitable carrier or vehicle in the form of an antimicrobial composition. The carrier is typically a liquid, solid, gel or paste. In various embodiments, the composition contains about 0.1 wt % to about 20 wt % of the antimicrobial agent. In embodiments where the antimicrobial agent is used as food preservative, the antimicrobial agent is added or combined with the food product in an amount of less than 1 wt %. In one embodiment, the composition containing the antifungal agent is in the form of a topical liquid, lotion, cream or gel for applying topically to the skin of a patent in need of treatment with the antifungal agent. The antifungal composition is applied topically to the skin of a patient in an effective amount to kill or inhibit the growth of a fungus.

Examples of suitable carriers for the antimicrobial agent include water, glycerol, ethanol, mineral oil and the like. The composition can also contain suitable humectants such as sorbitols and polyethylene glycols depending on the intended use.

In other embodiments, the antimicrobial composition can contain binders or thickening agents such as silica precipitates, carboxymethylcellulose, carboxyvinyl polymers, xanthan gum and carrageenan gum. Suitable surfactants include sodium lauryl sulfate and dodecylbenzene sulfonate. Flavorants, fragrances and anti-caking agents, as known in the art, can also be included.

In one embodiment of the invention, a food product is produced containing an effective amount of the antimicrobial agent or antimicrobial composition. The antimicrobial agent is generally dispersed in the food product to inhibit the growth of microorganisms, mold and fungi. The antimicrobial agent can be used with a dispersing agent or emulsifier as needed to keep the antimicrobial agent dispersed or suspended in the food product. The antimicrobial agent can be suspended in or mixed with a suitable food compatible carrier. In other embodiments, the antimicrobial agent can be applied as a coating on the surface of the food product.

In one embodiment of the invention, the antimicrobial composition is an antifungal containing an effective amount of the antifungal agent for topically applying to the skin of a patient. The composition can be in the form of a liquid, lotion, cream or gel that can be applied directly to the skin and to scratches, abrasions and minor cuts. The antifungal agent can also be added to a cleanser such as a detergent, soap or other cleaning agent. The cleaner can be hand or body soap, a hard surface cleaner or laundry detergent containing an effective amount of the composition to inhibit or kill various bacteria and fungi.

The process of the invention inhibits the growth of microorganisms by contacting the microorganisms with an effective amount of the antimicrobial agent or by applying the antimicrobial agent to a base material or substrate where the microorganisms come in contact. The base material can be a food product or a solid surface. In one embodiment, the substrate is capable of supporting the growth of microorganisms. The effective amount of the antimicrobial agent can vary depending on the particular microorganism to be inhibited and expected concentration of the microorganisms to be encountered. The antimicrobial agent is typically used to provide a minimum inhibitory concentration (MIC) amount. In one preferred embodiment, the antimicrobial agent is obtained from a mixture of plant materials including *Origanum vulgare* L., *Thymus vulgaris* L., *Cinnamomum zeylanicum* Nees, *Rosmarinus officinalis* L., *Lavandula officinalis* L., and *Hydrastis canadensis* L. In one embodiment, the plant materials are used in substantially equal amounts. The antimicrobial agent containing the mixture of the plant materials have an MIC about 1.5 µl/ml or less for gram-negative and gram-positive bacteria. The antimicrobial agent has an MIC of 1.5 µl/ml or less for *E. coli*, an MIC of 0.75 µl/ml or less for *Klebsiella pneumoniae*, and an MIC of 0.5 µl/ml for *Mycobacterium*. In one embodiment, the composition contains an effective amount of an antifungal agent consisting essentially of these plant materials or extracts which is effective in inhibiting or killing pathogenic dermatophytes such as *Epidermophyton floccosum, Trichophyton mentagrophytes* and *Microsporum canis*.

The growth of the microorganisms on a substrate is inhibited by contacting a substrate with the antimicrobial agent. The substrate can be a food product or other material that typically supports the growth of microorganisms. In other embodiments, the antimicrobial agent is dispersed within the substrate.

The antifungal and antimicrobial agent includes a mixture of the botanical materials in amounts and proportions to provide the desired antimicrobial properties and effectiveness in inhibiting the growth of the target microorganisms. The antifungal and antimicrobial agent of the invention includes the plant materials, extracts or essential oils to provide antifungal and antimicrobial inhibiting amounts of a compound selected from the group consisting of carvacrol, thymol, cinnamaldehyde, eugenol, cineole, camphor, α-pinene, rosmarinic acid, linalol, linalyl acetate, berberine and hydrastine, *Mentha piperita* L., *Citrus limon* L. and *Olea europaea* L., and mixtures thereof. Preferably, the antifungal and antimicrobial agent contains a mixture of the compounds or a mixture of the botanical materials in amounts to provide the antifungal and antimicrobial effect.

The antimicrobial agent can also be used to produce a shelf-stable composition where the composition includes a base material or substrate. The substrate can be a solid, liquid or semi-solid.

The antimicrobial agent of the invention has been found to be effective in inhibiting the growth of various bacteria and fungi. The effectiveness of the antimicrobial agent in many situations has been found to be at least as effective and under some conditions, more effective than conventional commercially available antimicrobial agents and preservatives in inhibiting the growth of bacteria and fungi on a substrate. In the following examples, the antimicrobial agent is shown to have a lower Minimum Inhibitory Concentration (MIC) than standard preservatives, antibacterial agents for certain gram-positive and gram-negative organisms and antifungal agents. The Minimum Inhibitory Concentration refers to the minimum concentration in micrograms per milliliter of an antimicrobial agent at which no bacteria or microorganism growth are observed. At concentrations at or above the Minimum Inhibitory Concentration, the antimicrobial agent is effective in killing or inhibiting the growth and reproduction of the microorganisms. At concentrations below the Minimum Inhibitory Concentration, the antimicrobial agent is not effective in inhibiting the growth of microorganisms.

It has been observed that the combination of botanical materials or extracts of *Origanum vulgare* L., *Thymus vulgaris* L., *Cinnamomum zeylanicum* Nees, *Rosmarinus officinalis* L., *Lavandula officinalis* L., and *Hydrastis canadensis* L. have a lower MIC than the conventional preservatives such as phenyloxyethanol, phenylethyl alcohol, and a mixture of methylparabens/propylparabens in a ratio of 5:4. The antimicrobial agent of the invention has been found to have a MIC of 3.0 µl/ml for gram-positive *Staphylococcus aureus*, gram-negative *Escherichia coli, Salmonella typhimurium, Klebsiella pneumoniae*, and *Pseudomonas aeruginosa*, acid-fast bacterium *Mycobacterium smegmatis* (similar to *M. tuberculosis*), the yeast *Candida albicans*, and the filamentous mold *Aspergillus niger*. Antifungal agents of the invention have an MIC of as low as 0.03 µl/ml for *Epidermophyton floccosum, Trichophyton mentagrophytes*, and *Microsporum canis*. The following non-limiting examples demonstrate the effectiveness of the antimicrobial agent and compositions containing the antimicrobial agent.

EXAMPLE 1

An antifungal agent was prepared from a mixture of botanical extracts containing 30 wt % *Origanum vulgare* L., 30 wt % *Thymus vulgaris* L., 10 wt % *Cinnamomum zeylanicum* Nees, 20 wt % *Rosmarinus officinalis* L., about 9.998 wt % *Lavandula officinalis* L., and 0.002 wt % *Hydrastis canadensis* L. The leaves from the plant materials were macerated and the various compounds and oils extracted. The resulting extracts obtained from each plant material were combined to form the antifungal agent.

EXAMPLE 2

An antifungal and antimicrobial composition was prepared from a mixture of botanical extracts containing 33.3 wt % *Origanum vulgare* L., 33.3 wt % *Thymus vulgaris* L., 22.2 wt % *Rosmarinus officinalis* L., 0.002 wt % *Hydrastis canadensis* L., 0.001 wt % *Olea europaea* L., and the balance *Lavandula officinalis* L. The leaves of the plant materials were macerated and the various compounds extracted. The extracts obtained from each plant material were then combined to form the antifungal agent.

EXAMPLE 3

An antifungal and antimicrobial composition was prepared containing a mixture of botanical extracts containing 30 wt % *Origanum vulgare* L., 30 wt % *Thymus vulgaris* L., 22 wt % *Rosmarinus officinalis* L., 8 wt % *Cinnamomum zeylanicum* Nees, 0.002 wt % *Hydrastis canadensis* L., 0.001 wt % *Olea europaea* L., 0.5 wt % *Mentha piperita* L., 0.5 wt % *Citrus limon* L., and the balance *Lavandula officinalis* L. (about 9.9 wt %) The leaves of the plant materials were macerated and extracted to recover the active compounds. The extracts containing the active compounds were combined to form the antifungal agent.

EXAMPLE 4

In this Example, the antifungal agents of Examples 1-3 were tested and compared with known commercially available antifungal agents.

Fungal Isolates

The organisms used included *Epidermophyton floccosum* ATCC 52066, *Trichophyton mentagrophytes* ATCC 9533, and *Microsporum canis* ATCC 36299. The molds were cultured on Oatmeal Agar slants to allow for conidial formation and incubated for 7 days at 25° C. For each mold, 5 ml of sterile 0.85% NaCl was added to each slant, the culture surface was rubbed with a sterile wooden applicator stick, and the suspension was then transferred to a sterile tube. By comparison to the McFarland 0.5 turbidity standard, the suspension was adjusted by adding sterile 0.85% NaCl as necessary. The resulting suspension was c.$1\times10^8$ CFU/ml. Then 300 µl of organism suspension was added to 10 ml of sterile saline, diluting it to c.$1\times10^6$ CFU/ml.

Antifungal Agents

The antifungal properties of the agents of Examples 1-3 were compared to two antifungal active ingredients used in common over the counter topical preparations namely Clotrimazole {CLO, which is found in Lotrimin® (Registered Trade Mark of Schering Corporation) and Mycelex® (Miles, Inc. Consumer Health Care Products)} and Ciclopirox Olamine {CO, which is found in Loprox® (Hoechst-Roussel Pharmaceuticals, Inc.)}. The active compounds were purchased from Sigma Chemical Company, St. Louis, Mo., USA.

Preparation of Samples

The Macrodilution broth method was performed using serial two-fold dilutions of RPMI-1640 (Sigma) with L-glutamine but without sodium bicarbonate.

Six 18×150 tubes of RPMI-1640 were used for each organism tested. Starting with tube 1 containing 20 ml RPMI labeled as 0.250 µl/ml and then tubes 2 through 6 containing 10 ml RPMI labeled as 0.125 µl/ml, 0.06 µl/ml, 0.03 µl/ml, 0.015 µl/ml, and 0.008 µl/ml respectively.

1. 26 µl of each product of Examples 1-3 was added to 1000 µl DMSO. The final concentration of DMSO is kept below 1%.
2. 200 µl of the sample dilution (26 µl/ml) was added to tube 1 (20 ml of RPMI-1640) making an initial concentration of 0.250 µl/ml.
3. A serial dilution was performed, pipetting 10 ml from tube 1 to tube 2; continuing the dilution to tube 6.

For the Clotrimazole, Mycelex® and Ciclopirox Olamine, ten 18×150 tubes of RPMI-1640 were used for each organism tested. Starting with tube 1 containing 20 ml RPMI labeled 16 µg/ml and then tubes 2 through 10 containing 10 ml RPMI labeled as 8.0 µg/ml, 4.0 µg/ml, 2.0 µg/ml, 1.0 µg/ml, 0.50 µg/ml, 0.25 µg/ml, 0.125 µg/ml, 0.06 µg/ml and 0.03 µg/ml respectively.

1. 160 mg of active ingredient was added to 100 ml DMSO.
2. 200 µl of the sample dilution (1600 µg/ml) was added to tube 1 (20 ml of RPMI-1640) making an initial concentration of 16 µg/ml.
3. A serial dilution was performed, pipetting 10 ml from tube 1 to tube 2; continuing the dilution to tube 10.

Inoculation and Incubation

Once the tubes were arranged according to product, concentration and mold type, 300 µl of appropriate mold inoculum was added to each tube and the tubes were then placed in an incubator at 35° C. along with a purity plate for inoculum verification for each mold. The final mold inoculum level was c.1×10⁴ CFU/ml. As controls, one tube with 10 ml RPMI was used for the "Negative Control", and 3 tubes with 10 ml RPMI plus 300 µl mold inoculum were used for the positive controls (one for each mold).

Minimum Inhibitory Concentration (MIC)

When the positive control showed adequate growth (5 days for *E. floccosum, T. mentagropytes* and *M. canis*), the initial results were recorded in relation to the growth present in the control tubes. Final results were recorded after 7 days. Growth (G) was noted when there was full growth visible (i.e. the tube appeared as cloudy as the positive control tube). Partial activity (P) was recorded when the broth in the tube was less turbid than the positive control tube. No growth (I) was recorded when there was total inhibition and the broth in the tube appeared clear (in comparison with the negative control tube).

The MIC measures fungistatic activity as the lowest concentration that will inhibit growth of the mold. This result is usually recorded as complete inhibition (I) with the exception of Clotrimazole (an azole). The MIC for an azole is the lowest concentration capable of inhibiting 80% growth, which would be a result of partial inhibition (P), one dilution below full inhibition.

Minimum Fungicidal Concentration (MFC)

The MFC measures the lowest concentration of the test agent that will kill the fungi. The fungicidal activity of the products was determined by subculturing 20 µl from tubes with no visible growth onto properly labeled SDA plates. Also 20 µl from the last tube with growth and 20 µl from the positive control tube were subcultured as controls. All plates were incubated at 25° C. for 14 days. The MFC was recorded as the lowest concentration showing no growth or <3 colonies of growth, which equals 99-99.5% killing activity.

Results and Discussion

The MIC and MFC for Examples 1, 2 and 3 are 0.03 µl/ml, 0.125 µl/ml and 0.125 µl/ml, respectively. All species of the dermatophytes analyzed were not only inhibited but also killed by all three of the products of Examples 1-3 at concentrations of 0.125 µl/ml or less. The products of Examples 1-3 have minimum fungicidal concentrations comparable to, and not exceeding, twofold their MIC, demonstrating primary fungicidal activity.

Fungicidal properties are particularly important because the infectious part of the dermatophytes can remain in the skin scales for long periods of time. To eliminate infection by actually killing the mold and thus preventing recurrence, fungicidal products are far superior to fungistatic drugs. Also the minimum fungicidal concentration has the possibility of representing clinical outcome, and working with MFC has suggested that they may be more predictive than MIC. The MIC of Clotrimazole (CLO) and Ciclopirox Olamine (CO) are 0.06 µg/ml and 16.0 µg/ml, respectively. CLO and CO are fungistatic not fungicidal hence the MFC are not reported. So although less of these active ingredients are needed to inhibit the mold, they are unable to kill the dermatophytes even at concentrations greater than 4 µg/ml (6 fold MIC) for CLO and greater than 32 µg/ml (two fold MIC) for CO. The results obtained from the test are presented in Tables 1, 2, and 3.

Two safety tests were conducted for the products of Examples 1-3 using 1% (333 times the MIC/MFC), 2.75% (220 times the MIC/MFC) and 2.25% (180 times the MIC/MFC), respectively. The first test was an eye irritation test using the Hen's Egg Test-Utilizing the Chorioallantoic Membrane (HET-CAM). The second test was the 48 hours Patch Test (PT) to determine by epidermal contact the primary irritation potential of the test material using 57 subjects for the products of Examples 1 and 2 and 53 subjects for the product of Example 3. It was found that each of the 3 products at the concentrations used, had neither ocular irritation potential nor dermal irritation potential in vivo. Consequently, the products of Examples 1-3 possess all the criteria pertinent to an ideal natural alternative to synthetic antifungal agents with fungicidal activity.

TABLE 1

Antifungal Screening Results

| Organism | Test | 0.250 | 0.125 | 0.06 | 0.03 | 0.015 | 0.008 | Negative control | Positive control |
|---|---|---|---|---|---|---|---|---|---|
| Concentration of the Product of Example 1 (µl/ml) | | | | | | | | | |
| *Epidermophyton floccosum* ATCC 52066 | MIC | I | I | I | I | P | G | CLEAR | CLOUDY |
| | MFC | I | I | I | I | P | G | NO GROWTH | GROWTH |
| *Trichophyton mentagrophytes* ATCC 9533 | MIC | I | I | I | I | P | G | CLEAR | CLOUDY |
| | MFC | I | I | I | I | P | G | NO GROWTH | GROWTH |
| *Microsporum canis* ATCC 36299 | MIC | I | I | I | I | I | G | CLEAR | CLOUDY |
| | MFC | I | I | I | I | I | G | NO GROWTH | GROWTH |
| Concentration of the Product of Example 2 (µl/ml) | | | | | | | | | |
| *Epidermophyton floccosum* ATCC 52066 | MIC | I | I | I | G | G | G | CLEAR | CLOUDY |
| | MFC | I | I | I | G | G | G | NO GROWTH | GROWTH |
| *Trichophyton mentagrophytes* ATCC 9533 | MIC | I | I | G | G | G | G | CLEAR | CLOUDY |
| | MFC | I | I | G | G | G | G | NO GROWTH | GROWTH |
| *Microsporum canis* ATCC 36299 | MIC | I | I | P | G | G | G | CLEAR | CLOUDY |
| | MFC | I | I | G | G | G | G | NO GROWTH | GROWTH |
| Concentration of the Product of Example 3 (µl/ml) | | | | | | | | | |
| *Epidermophyton floccosum* ATCC 52066 | MIC | I | I | P | G | G | G | CLEAR | CLOUDY |
| | MFC | I | I | G | G | G | G | NO GROWTH | GROWTH |

TABLE 1-continued

Antifungal Screening Results

| Organism | Test | 0.250 | 0.125 | 0.06 | 0.03 | 0.015 | 0.008 | Negative control | Positive control |
|---|---|---|---|---|---|---|---|---|---|
| Trichophyton mentagrophytes ATCC 9533 | MIC | I | I | I | G | G | G | CLEAR | CLOUDY |
| | MFC | I | I | I | G | G | G | NO GROWTH | GROWTH |
| Microsporum canis ATCC 36299 | MIC | I | I | I | P | P | G | CLEAR | CLOUDY |
| | MFC | I | I | I | G | G | G | NO GROWTH | GROWTH |

Minimum Inhibitory Concentration (MIC)/Minimum Fungicidal Concentration (MFC)
Abbreviations: G = growth, P = partial inhibition, I = inhibition (no growth).
Results are scored in relation to the growth present in the negative control tube.

TABLE 2

Antifungal Screening Results of Active Ingredients

| | 16.0 | 8.0 | 4.0 | 2.0 | 1.0 | 0.50 | 0.250 | 0.125 | 0.06 | 0.03 | negative | positive |
|---|---|---|---|---|---|---|---|---|---|---|---|---|
| Concentration of Clotrimazole (CLO) (µg/ml) | | | | | | | | | | | | |
| E. floccosum ATCC52066 | I | I | I | I | I | I | I | I | P | G | clear | cloudy |
| T. mentagrophytes ATCC9533 | I | I | I | I | I | I | I | I | P | P | clear | cloudy |
| M. canis ATCC36299 | I | I | I | I | I | I | I | I | P | P | clear | cloudy |
| Concentration of Ciclopirox Olamine (CO) (µg/ml) | | | | | | | | | | | | |
| E. floccosum ATCC52066 | I | I | G | G | G | G | G | G | G | G | clear | cloudy |
| T. mentagrophytes ATCC9533 | I | P | G | G | G | G | G | G | G | G | clear | cloudy |
| M. canis ATCC36299 | I | I | P | G | G | G | G | G | G | G | clear | cloudy |

Minimum Inhibitory Concentration (MIC)
Abbreviations: G = growth, P = partial inhibition, I = inhibition (no growth).
Results are scored in relation to the growth present in the positive control tube.

TABLE 3

Minimum Inhibitory Concentrations Summarized

| | Example 1 (µl/ml) | Example 2 (µl/ml) | Example 3 (µl/ml) | Clotrimazole CLO (µg/ml) | Ciclopirox Olamine CO (µg/ml) |
|---|---|---|---|---|---|
| Epidermophyton floccosum ATCC 52066 | 0.03 | 0.06 | 0.125 | 0.06 | 8.0 |
| Trichophyton mentagrophytes ATCC 9533 | 0.03 | 0.125 | 0.06 | 0.06 | 16.0 |
| Microsporum canis ATCC 36299 | 0.03 | 0.125 | 0.06 | 0.06 | 4.0 |
| MIC to Inhibit all organisms | 0.003% | 0.0125% | 0.0125% | 0.000006% | 0.0016% |
| MFC to Inhibit all organisms | 0.003% | 0.0125% | 0.0125% | N/A | N/A |

EXAMPLE 5

The Agar Dilution susceptibility method was used to test the effectiveness of the antimicrobial composition of Example 1. The organisms used were S. aureus ATCC 29213, E. coli ATCC 25922, S. typhimurium ATCC 14028, K. pneumoniae ATCC 10031, P. aeruginosa ATCC 27853, C. albicans ATCC 10231, and M. smegmatis ATCC 14468. The organisms were maintained on Tryptic Soy Agar (TSA) slants. For each week, the organisms were cultured in 10 ml of Tryptic Soy Broth (TSB). After incubation at 37° C. for 17 hours (48 hours for M. smegmatis), the organism suspensions were diluted with 10 ml of sterile saline as shown in Table 4. The mold Aspergillus niger was sustained on a Sabouraud Dextrose Agar slant. The sample was then cultured in 10 ml of Tryptic Soy Broth and incubated for 7 days at 22° C. The mold was then diluted in 0.1% Tween 80 in saline. The diluted bacteria and yeast organisms were then inoculated onto the prepared sample plates with a 1 µl loop. The mold Aspergillus niger was added to prepared sample tubes with a 100 µl pipette.

TABLE 4

Microorganism Dilutions

| | |
|---|---|
| S. aureus ATCC 29213 | 100 µl susp/10 ml saline |
| E. coli ATCC 25922 | 100 µl susp/10 ml saline |
| S. typhimurium ATCC 14028 | 100 µl susp/10 ml saline |
| K. pneumoniae ATCC 10031 | 100 µl susp/10 ml saline |
| M. smegmatis ATCC 14468 | Undiluted |
| C. albicans ATCC 10231 | 1 ml susp/10 ml saline |
| P. aeruginosa ATCC 27853 | 1 µl susp/10 ml saline |
| A. niger ATCC 16404 | 1 ml susp/10 ml 0.1% Tween 80 in saline |

Phenyloxyethanol (PE), phenylethyl alcohol (PEA) and methyl/propylparabens (MP) in a ratio of 5:4 were initially screened at their commonly recommended effective concentrations of 0.3% v/v (3 µl/ml); 1% v/v (10 µl/ml); and 0.18% w/v (1 mg methyl and 0.8 mg propylparaben/ml), respectively. The antimicrobial agent was used at an initial concentration of 0.15% v/v (1.5 µl/ml).

The sample plates for the bacteria and yeast were prepared as follows:

Prepare 10 ml tubes of TSA and allow to cool to 50° C.,
Add the calculated amount of the preservative or antimicrobial agent to 100 µl dimethylsulfoxide (DMSO) to achieve the specified concentration per ml TSA when 100 µl of the DMSO solution are added to a test tube containing 10 ml of TSA,
Vortex to homogenize the mixture in TSA,
Pour TSA and the preservative or antimicrobial agent into a properly labeled Petri dish,
Allow to cool overnight at room temperature.

The sample for the mold *Aspergillus niger* was prepared as follows:

Prepare 10 ml tubes of Tryptic Soy Broth (TSB),
Add the calculated amount of the sample to 100 µl dimethylsulfoxide (DMSO) to achieve the specified concentration per ml TSB. Then 100 µl of the DMSO is added to a test tube containing 10 ml of TSB,
Vortex to homogenize the mixture in TSB,
Add 100 µl of *Aspergillus niger* suspension to a tube of TSB not inoculated with any sample as a positive control.

The prepared sample plates were divided into seven sections and the plates labeled according to the preservative or antimicrobial agent. Each section was labeled according to the microorganism to be applied to each section. The diluted organism suspensions were inoculated onto their appropriate section with a 1 µl loop, streaking radially from the center to the outer edge of the plate. A positive control plate was prepared without a preservative or antimicrobial agent of Example 1. The plates were then incubated at 37° C. for 48 hours, recording the results at 24 and 48 hours.

The prepared sample tubes were inoculated with 100 µl of the mold *Aspergillus niger* suspension to produce a final mold spore concentration in each sample tube of 1×10$^4$ to 1×10$^5$ spores/ml. The prepared sample tubes of TSB were incubated at 37° C. for 5 days with the results being recorded at 3 and 5 days.

The results for the bacteria and yeast were scored in relation to the growth present on the positive control plate. Growth (G) was noted when there was full growth visible and the organism was not affected. Partial activity (P) was recorded when the organism was morphologically altered or growth was partially inhibited, and no growth (I) was recorded when there was total inhibition. The results are recorded in Table 5.

The results for *Aspergillus niger* were scored in relation to the growth present in the positive control tube. The growth (G) was noted when there was full growth visible as determined by the tube appearing cloudy to the same extent as the positive control tube. Partial activity (P) was recorded when the sample tube of TSB was less turbid than the control tube. No growth (I) was recorded when there was total inhibition and broth in the tube appeared clear.

When a result of (I) was scored, the MIC was established by performing the dilutions as indicated in Table 5 and Table 6. In this example and the tables, the amount of the antimicrobial agent is expressed in terms of the volume of antimicrobial sample. The concentration of the antimicrobial agent of 1 µl/ml corresponds to 1 mg (milligram)/ml of the antimicrobial agent. The MIC obtained was confirmed by three consecutive results. DMSO was used to solubilize the test samples and help to diffuse the lipophilic ingredients into the agar. DMSO was used at a concentration not exceeding 1%.

TABLE 5

Antimicrobial Screening Results

| SAMPLE/ml of Agar or Broth | MICROORGANISMS* | | | | | | | |
|---|---|---|---|---|---|---|---|---|
| | 1 | 2 | 3 | 4 | 5 | 6 | 7 | 8 |
| Antimicrobial Agent of Example 1 | | | | | | | | |
| 0.25 µl/ml | G | G | G | G | P | P | G | G |
| 0.5 µl/ml | G | G | G | P | I | I | G | P |
| 0.75 µl/ml | P | G | G | P | I | I | G | I |
| 1.0 µl/ml | I | I | I | I | I | I | P | I |
| 1.5 µl/ml | I | I | I | I | I | I | P | I |
| 2.0 µl/ml | I | I | I | I | I | I | I | I |
| 3.0 µl/ml | I | I | I | I | I | I | I | I |
| Phenoxyethanol (PE) | | | | | | | | |
| 1.0 µl/ml | G | G | G | G | P | P | P | P |
| 2.5 µl/ml | G | P | P | P | I | I | P | I |
| 3.0 µl/ml | G | P | P | P | I | I | I | I |
| 5.0 µl/ml | G | I | I | I | I | I | I | I |
| 10.0 µl/ml | I | I | I | I | I | I | I | I |
| Phenylethyl Alcohol (PEA) | | | | | | | | |
| 0.75 µl/ml | G | G | G | G | G | P | P | G |
| 1.5 µl/ml | G | P | P | I | P | P | P | P |
| 3.0 µl/ml | G | I | I | I | I | I | P | I |
| 5.0 µl/ml | P | I | I | I | I | I | I | I |
| 6.0 µl/ml | I | I | I | I | I | I | I | I |
| Methylparaben and Propylparaben (MP) | | | | | | | | |
| 0.9 mg/ml | G | G | G | G | G | G | G | G |
| 1.8 mg/ml | G | G | G | G | G | G | G | P |
| 3.6 mg/ml | G | G | G | G | G | G | G | I |
| 5.4 mg/ml | P | G | G | G | I | I | P | I |
| 7.2 mg/ml | P | P | P | P | I | I | P | I |
| 10.8 mg/ml | I | P | P | I | I | I | P | I |
| 16.2 mg/ml | I | I | P | I | I | I | P | I |
| 21.6 mg/ml | I | I | I | I | I | I | I | I |

Abbreviations: G = growth, P = partial inhibition, I = inhibition (no growth)
Results are scored in relation to the growth present on the negative control plate.
*Microorganisms: (1) *Staphylococcus aureus* (2) *Escherichia coli* (3) *Salmonella typhimurium* (4) *Klebsiella pneumoniae* (5) *Mycobacterium smegmatis* (6) *Candida albicans* (7) *Pseudomonas aeruginosa* (8) *Aspergillus niger*

TABLE 6

Minimum Inhibitory Concentration (MIC)
(sample/ml of agar or broth)

| | Antimicrobial Agent of Example 1 | Phenoxyethanol | Phenylethyl Alcohol | Methylparaben & Propylparaben |
|---|---|---|---|---|
| S. aureus ATCC 25213 | 1.0 µl/ml | 10.0 µl/ml | 10.0 µl/ml | 10.8 mg/ml |
| E. coli ATCC 25922 | 1.0 µl/ml | 5.0 µl/ml | 5.0 µl/ml | 16.2 mg/ml |
| S. typhimurium ATCC 14028 | 1.0 µl/ml | 5.0 µl/ml | 5.0 µl/ml | 21.6 mg/ml |
| K. Pneumoniae ATCC 10031 | 1.0 µl/ml | 5.0 µl/ml | 5.0 µl/ml | 10.8 mg/ml |
| M. smegmatis ATCC 14468 | 0.5 µl/ml | 2.5 µl/ml | 2.5 µl/ml | 5.4 mg/ml |
| C. albicans ATCC 10231 | 0.5 µl/ml | 2.5 µl/ml | 2.5 µl/ml | 5.4 mg/ml |
| P. aeruginosa ATCC 27853 | 2.0 µl/ml | 5.0 µl/ml | 5.0 µl/ml | 21.6 mg/ml |
| A. niger ATCC 16404 | 0.75 µl/ml | 2.5 µl/ml | 2.5 µl/ml | 3.6 mg/ml |

The Minimum Inhibitory Concentrations for the antimicrobial agent of Example 1 and the other preservatives tested on each individual microorganism are presented in Table 6. The antimicrobial agent of Example 1 has the lowest MIC (2.0 µl (0.2%)/ml) capable of inhibiting all the tested organisms (i.e., gram-positive, gram-negative, acid-fast bacteria and yeast). Only 2.0 µl (0.2%)/ml were required to inhibit all microorganisms tested except *S. typhimurium* and 1.5 µl (0.15%)/ml was found to inhibit all microorganisms except *P. aeruginosa* and *S. typhimurium*. Much higher concentrations of the other preservatives were required to inhibit all microorganisms tested. Complete inhibition of all of the microorganisms tested required 6.0 µl (0.6%)/ml of PEA, 10.0 µl (1%)/ml of PE and more than 7.2 mg (0.72%)/ml of MP (its MIC was found later to be 21.6 mg (2.16%)/ml).

The antimicrobial agent of the invention has been found to be effective in inhibiting the growth of *Staphylococcus aureus* (*S. aureus*) at a MIC of 1.5 µl (0.15%)/ml. Many other known preservatives such as phenoxyethanol require four times this amount to inhibit the growth of *S. aureus*. Phenylethyl alcohol is commonly used at 0.3 wt % and methylparaben and propylparaben mixtures are commonly used as 0.18 wt %. These conventional preservatives at these concentrations have been found to have no effect on *S. aureus*. *S. aureus* is frequently part of the normal human flora and is a common pathogen that causes skin infections, food poisoning, and toxic shock syndrome.

*E. coli*, *S. typhimurium* and *K. Pneumoniae* are gram-negative rods that cause gastroenteritis and a variety of infections in humans. The antimicrobial agent of the invention has been found to inhibit the growth of these microorganisms at low concentrations compared with conventional preservatives. For example, *K. Pneumoniae* is inhibited at a concentration of 0.75 µl (0.075%)/ml, *E. coli* is inhibited at a concentration of 1.5 µl (0.15%)/ml and *S. typhimurium* is inhibited at a concentration of 3.0 µl (0.3%)/ml.

*M. smegmatis* is an acid-fast bacterium similar to *M. tuberculosis*, which is a highly communicable intercellular parasitic bacterium that is always associated with infection. The antimicrobial agent of Example 1 is able to inhibit the acid-fast bacterium at a concentration of 0.5 µl (0.05%)/ml while other preservatives needed a concentration ranging from 5 to 10 times higher.

*C. albicans* is the species of yeast most often isolated from clinical specimens and can cause infection of the skin, nails and mucous membranes. It is also a source of diaper rash, certain vaginal and gastrointestinal infections. The antimicrobial agent of Example 1 was able to inhibit the yeast at a concentration lower than 0.5 µl (0.05%)/ml while PE, PEA and MP could inhibit it at concentrations ranging from 5 to 10 times higher.

EXAMPLE 6

The mold *Aspergillus niger* ATCC 16404 was selected for the antifungal testing and maintained on Sabouraud Dextrose Agar. *Aspergillus niger* is a mold that commonly causes opportunistic infections in humans. Spores are prevalent in soil and on decaying organic matter. *Aspergillus niger* is also a common cause of contamination in products. The organism was cultured in 10 ml of Tryptic Soy Broth for 7 days at 22° C. After incubation, 1 ml of mold culture was added to 10 ml of 0.1% Tween 80 solution in sterile saline to achieve a spore concentration of 0.5 McFarland ($1 \times 10^8$ spores/ml). This concentration was determined by visual comparison to a 0.5 McFarland standard. The macro-dilution broth susceptibility method was utilized to limit the amount of airborne mold spores by suspending them in liquid in a capped test tube as opposed to the agar dilution method used in previous research.

The antimicrobial agent of Example 1 and preservatives phenoxyethanol, phenylethyl alcohol and methyl and propyl parabens (5:4) were initially screened at a concentration of 0.1%. The samples were prepared as follows:

Prepare 10 ml tubes of Tryptic Soy Broth (TSB).

Add sample to 100 µl of DMSO (dimethylsulfoxide) to achieve specified concentration. (11 µl sample+100 µl DMSO for 0.1% concentration).

Pipette 100 µl of preservatives in DMSO into one 10 ml tube TSB.

Vortex to homogenize mixture in TSB.

Add 100 µl of *A. niger* suspension to each of the tubes.

Add 100 µl of *A. niger* suspension to a tube of TSB without a preservative as a negative control sample.

The final concentration of mold spores in each sample was $1 \times 10^4 - 1 \times 10^5$ spores/ml. The prepared tubes of TSB were incubated at 37° C. for 5 days, and the results recorded at 3 and 5 days.

Each sample was tested for antifungal activity against *Aspergillus niger*. Concentrations were increased or decreased to determine the minimum inhibitory concentration (MIC) of each sample. When a MIC had been reached, the sample was tested multiple times at that concentration to confirm the result.

The results were scored in relation to the growth present in the negative control tube. Growth (G) was noted when there was full growth visible (i.e., the tube appeared as cloudy as the negative control tube). Partial activity (P) was recorded when the sample tube of TSB was less turbid than the control tube, and now growth (I) was recorded when there was total inhibition and the broth in the tube appeared clear. When a result of (I) was scored, the MIC was established by performing the appropriate dilutions. The results are recorded in the following Table 7.

TABLE 7

Antifungal Screening Results
*Aspergillus niger* ATCC 16404

|  | 0.25 µl/ml | 0.5 µl/ml | 0.75 µl/ml | 1.0 µl/ml | 1.5 µl/ml | 2.5 µl/ml |
|---|---|---|---|---|---|---|
| Antimicrobial Agent of Example 1 | G | P | I | I | I | I |
| Phenoxyethanol | G | G | G | P | P | I |
| Phenylethyl Alcohol | G | G | G | P | P | I |

|  | 0.9 µl/ml | 1.8 µl/ml | 2.7 µl/ml |
|---|---|---|---|
| Methyl/Propylparaben | G | P | I |

Abbreviations: G = growth, P = partial inhibition, I = inhibition (no growth).
Results are scored in relation to the growth present in the negative control tube.

The result for the minimum inhibitory concentrations against fungi for the antimicrobial agent of Example 1 and the preservatives are presented in Table 8. The antimicrobial agent of Example 1 is shown to have the lowest MIC (0.75 μl/ml) capable of inhibiting the *Aspergillus niger*.

TABLE 8

Minimum Inhibitory Concentration (MIC)

|  | Antimicrobial Agent of Example 1 | Phenoxyethanol | Phenylethyl Alcohol | Methylparaben & Propylparaben |
|---|---|---|---|---|
| *A. niger* ATCC 16404 | 0.75 μl/ml | 2.5 μl/ml | 2.5 μl/ml | 2.7 μl/ml |
| *C. albicans*\* ATCC 10231 | 0.5 μl/ml | 2.5 μl/ml | 3.0 μl/ml | 5.4 μl/ml |

The yeast *C. albicans* was tested in a previous trial and is presented herein to express the total antifungal properties of each sample

*Aspergillus niger* is a rapid growing filamentous mold whose spores are ubiquitous in nature. Therefore, it is a common fungal contaminant, and an opportunistic pathogen in humans. It may also cause black mold rot on a variety of fruits and vegetables.

EXAMPLE 7

An antimicrobial agent was prepared from a mixture containing 0.002 wt % *Hydrastis canadensis* L., 0.001 wt % *Olea europaea*, 33.3 wt % *Origanum vulgare* L. extract, 33.3 wt % *Thymus vulgaris* L. extract, 22.2 wt % *Rosmarinus officinalis* L. extract, and the balance *Lavandula officinalis* L. extract (about 8.99 wt %).

The antimicrobial activity of this composition was determined using the Agar Dilution susceptibility test. The microorganism samples and agar samples were prepared in the same manner as in Example 5. The test results and MIC were determined according to the method of Example 5. The test results are shown in Tables 9 and 10.

TABLE 9

| SAMPLE/ml of Agar | MICROORGANISMS\* | | | | | | | |
|---|---|---|---|---|---|---|---|---|
| | 1 | 2 | 3 | 4 | 5 | 6 | 7 | 8 |
| 0.5 μl/ml | G | G | G | G | G | G | G | G |
| 0.75 μl/ml | G | G | G | G | P | G | G | P |
| 1.0 μl/ml | G | G | G | I | I | I | G | I |
| 1.5 μl/ml | P | G | G | I | I | I | G | I |
| 2.0 μl/ml | I | I | P | I | I | I | G | I |
| 3.0 μl/ml | I | I | P | I | I | I | P | I |
| 3.5 μl/ml | I | I | I | I | I | I | P | I |
| 4.0 μl/ml | I | I | I | I | I | I | P | I |
| 4.5 μl/ml | I | I | I | I | I | I | P | I |
| 5.0 μl/ml | I | I | I | I | I | I | P | I |
| 5.5 μl/ml | I | I | I | I | I | I | I | I |

Abbreviations: G = growth, P = partial inhibition, I = inhibition (no growth)
Results are scored in relation to the growth present on the negative control plate.
\*Microorganisms: (1) *Staphylococcus aureus* (2) *Escherichia coli* (3) *Salmonella typhimurium* (4) *Klebsiella pneumoniae* (5) *Mycobacterium smegmatis* (6) *Candida albicans* (7) *Pseudomonas aeruginosa* (8) *Aspergillus niger*

TABLE 10

Minimum Inhibitory Concentration (MIC)
(sample/ml of agar or broth)

|  | Antimicrobial Agent of Example 4 |
|---|---|
| *S. aureus* ATCC 25213 | 2.0 μl/ml |
| *E. coli* ATCC 25922 | 2.0 μl/ml |
| *S. typhimurium* ATCC 14028 | 3.5 μl/ml |
| *K. Pneumoniae* ATCC 10031 | 1.0 μl/ml |
| *M. smegmatis* ATCC 14468 | 1.0 μl/ml |
| *C. albicans* ATCC 10231 | 1.0 μl/ml |
| *P. aeruginosa* ATCC 27853 | 5.5 μl/ml |
| *A. niger* ATCC 16404 | 1.0 μl/ml |

While various embodiments have been selected to demonstrate the invention, it will be understood that various changes and modifications can be made without departing from the scope of the invention as defined in the appended claims.

What is claimed is:

1. A process for inhibiting the growth of fungus, said process comprising the step of applying an effective amount of an antifungal agent to the fungus, said antifungal agent including a mixture of plant materials comprising about 20 wt % to about 40 wt % *Origanum vulgare* L., about 20 wt % to about 40 wt % *Thymus vulgaris* L., about 10 wt % to about 30 wt % *Rosmarinus officinalis* L., and about 5 wt % to about 15 wt % *Lavandula officinalis* L. wherein each of said plant materials is included in an amount effective to provide an antifungal effect and where the percentages are based on the total weight of the antifungal agent.

2. The process of claim 1, wherein said antifungal agent further comprises about 5 wt % to 15 wt % *Cinnamomum zeylanicum* Nees.

3. The process of claim 1, wherein said antifungal agent further comprises *Hydrastis canadensis* L.

4. The process of claim 1, wherein said fungus is selected from the group consisting of pathogenic *Epidermophyton*, *Trichophyton*, and *Microsporum*.

5. The process of claim 1, wherein said antifungal agent comprises at least 30 wt % *Origanum vulgare* L., and at least 30 wt % *Thymus vulgaris* L. and at least 20 wt % *Rosmarinus officinalis* L., based on the total weight of the antifungal agent.

6. The process of claim 5, wherein said antifungal agent further comprises at least 10 wt % *Cinnamomum zeylanicum* Nees based on the total weight of the antifungal agent.

7. The process of claim 1, wherein said antifungal agent comprises at least 10 wt % *Lavandula officinalis* L.

8. The process of claim 7, wherein said antifungal agent further comprises about 0.001 wt % to about 0.005 wt % *Olea europaea* L.

9. The process of claim 1, wherein said antifungal agent is dispersed in an aqueous camer.

10. The process of claim 1, wherein said antifungal agent further comprises *Olea europaea* L., *Mentha piperita* L. and *Citrus Limon* L.

11. The process of claim 1, wherein said plant materials are plant extracts and are included in amounts effective to provide an antifungal effect.

12. The process of claim 1, wherein said plant materials are present in effective amounts to provide an antifungal amount of a compound selected from the group consisting of carvacrol, thymol, cinnamaldehyde, eugenol, cineole, camphor, α-pinene, rosmarinic acid, linalol, linalyl acetate, berberine and hydrastine, and mixtures thereof.

13. A process for treating dermatophytes on the skin or nail of an animal, said process comprising the steps of:

topically contacting the dennatophytes on the skin or nail of an animal in need thereof with an antifungal composition including an effective amount of an antifungal agent, said antifungal agent comprising a mixture of about 20 wt % to 40 wt % *Origanum vulgare* L., about 20 wt % to 40 wt % *Thymus vulgaris* L., about 10 wt % to 30 wt % *Rosmarinus officinalis* L., *Lavandula officinalis* L., *Hydrastis canadensis* L, and *Olea europaea*, where the percentages are based on the total weight of the antifungal agent.

14. The process of claim 13, wherein said antifungal composition further comprises an aqueous camer.

15. The process of claim 13, wherein said antifungal agent further comprises *Cinnamomum zeylanicum* Nees.

16. The process of claim 13, wherein said antifungal agent comprises at least 30 wt % *Origanum vulgare* L., at least 30 wt % *Thymus vulgaris* L., and at least 20 wt % *Rosmarinus officinalis* L.

17. The process of claim 13, wherein said antifungal agent further comprises about 5 wt % to 15 wt % *Cinnamomum zeylanicum* Nees in an amount effective to provide an antifungal effect.

18. The process of claim 13, wherein said antifungal agent further comprises about 1 wt % to 5 wt % *Mentha piperita* L. and about 1 wt % to 5 wt % *Citrus Limon* L.

19. The process of claim 13, wherein said dermatophytes are selected from the group consisting of *Epidermophyton, Trichophyton*, and *Microsporum*.

20. An antidermatophytic composition, comprising:

an antidermatophytic agent comprising a mixture of plant material extracts of about 20 wt % to 40 wt % *Origanum vulgare* L., about 20 wt % to 40 wt % *Thymus vulgaris* L., about 10 wt % to 30 wt % *Rosmarinus officinalis* L., and about 5 wt % to 15 wt % *Lavandula officinalis* L. in amounts effective to provide an antidermatophytic effect when applied topically to an animal, and a carrier for said antidermatophytic agent, wherein said antidermatophytic agent is present in said carrier in an amount effective to provide an antifungal effect.

21. The composition of claim 20, wherein said antidermatophytic agent is effective in inhibiting the growth of *Epidermophyton, Trichophyton*, and *Microsporum*.

22. The composition of claim 20, wherein said carrier is an aqueous carrier.

23. The composition of claim 20, wherein said plant materials are present in amounts to provide a dermatophytic inhibiting amount of a compound selected from the group consisting of carvacrol, thymol, cinnamaldehyde, eugenol, cineole, camphor, α-pinene, rosmarinic acid, linalol, linalyl acetate, berberine and hydrastine, and mixtures thereof.

24. The composition of claim 20, wherein said antidermatophytic agent further comprises about 0.001 wt % to about 0.005 wt % *Olea europaea* L.

25. The composition of claim 24, wherein said antidermatophytic agent comprises about 5 wt % to 15 wt % *Cinnamomum zeylanicum* Nees.

26. The composition of claim 20, wherein said antidermatophytic agent consists essentially of *Origanum vulgare* L., *Thymus vulgaris* L., *Cinnamomum zeylanicum* Nees, *Rosmarinus officinalis* L., *Lavandula officinalis* L., *Hydrastis canadensis* L.

27. The composition of claim 20, wherein said antidermatophytic agent consists essentially of *Origanum vulgare* L., *Thymus vulgaris* L., *Cinnamomum zeylanicum* Nees, *Rosmarinus officinalis* L., *Lavandula officinalis* L., *Hydrastis canadensis* L., *Olea europaea* L., *Mentha piperita* L. and *Citrus Limon* L.

* * * * *